United States Patent [19]

Chapman

[11] 4,108,667

[45] Aug. 22, 1978

[54] PHOTOGRAPHIC COMPOSITIONS AND ELEMENTS CONTAINING BENZO[A]QUINOLIZINIUM METHINE DYES

[75] Inventor: Derek D. Chapman, Rochester, N.Y.

[73] Assignee: Eastman Kodak Company, Rochester, N.Y.

[21] Appl. No.: 723,873

[22] Filed: Sep. 16, 1976

Related U.S. Application Data

[63] Continuation-in-part of Ser. No. 556,499, Mar. 7, 1975, abandoned.

[51] Int. Cl.$^2$ .............................................. G03C 1/16
[52] U.S. Cl. ...................................... 96/131; 96/135; 96/136; 96/137; 96/138; 96/140; 96/141; 542/471; 542/454; 542/465
[58] Field of Search ................. 96/131, 135, 136, 137, 96/140, 141

[56] References Cited

U.S. PATENT DOCUMENTS

| | | | |
|---|---|---|---|
| 3,408,195 | 10/1968 | Oliver | 96/136 |
| 3,772,034 | 11/1973 | Fumia | 96/135 |
| 3,880,844 | 4/1975 | Fumia | 96/135 |
| 4,003,750 | 1/1977 | Haseltine et al. | 96/136 |

OTHER PUBLICATIONS

Research Disclosure 11213, Aug., 1973.

*Primary Examiner*—J. Travis Brown
*Attorney, Agent, or Firm*—J. G. Levitt

[57] ABSTRACT

The invention relates to methine dyes and photographic silver halide compositions and film elements comprising methine dyes which contain 9,9a-dihydropyrido-[1,2-a]indolium nuclei, benzo[a]quinolizinium nuclei or 6,7-dihydrobenzo[a]quinolizinium nuclei.

4 Claims, No Drawings

PHOTOGRAPHIC COMPOSITIONS AND ELEMENTS CONTAINING BENZO[A]QUINOLIZINIUM METHINE DYES

This application is a continuation-in-part of U.S. application Ser. No. 556,499, filed Mar. 7, 1975, now abandoned.

This invention relates to light sensitive photographic silver halide compositions and elements which contain novel dyes.

Lincoln et al. U.S. Pat. No. 3,282,932 issued on Nov. 1, 1966 describes merocyanine, styryl and hemicyanine dyes prepared using N,α-alkylene cycloammonium quaternary salts as intermediates. Carbocyanine dyes having a protonated nitrogen containing heterocyclic ring are described in Kalenda U.S. Pat. No. 3,173,791 issued Mar. 16, 1965 and in Oliver U.S. Pat. No. 3,408,195 issued on Oct. 29, 1968. There is no suggestion in these patents of methine dyes prepared using the new heterocyclic quaternary salts described hereinafter or the preparation of such dyes and quaternary salts.

Quaternary salts having a pyrido[1,2-a]indole nucleus and methods of preparing the salts are disclosed in *Research Disclosure* published August 1973 at 11213. Sensitizing dyes prepared from the pyrido[1,2-a]indole quaternary salts are described in U.S. patent application Ser. No. 356,980 filed May 3, 1973 and presently copending herewith.

In accordance with this invention, methine dyes are provided which contain a 9,9a-dihydropyrido[1,2-a]indolium nucleus, a benzo[a]quinolizinium nucleus or a 6,7-dihydrobenzo[a]quinolizinium nucleus. The dyes are typically cyanine or merocyanine dyes and, hence the inventive nuclei are joined through a methine linkage to a nucleus of the type used in such dyes.

The methine dyes of this invention can contain nuclei derived from compounds having one of the following structural formulae:

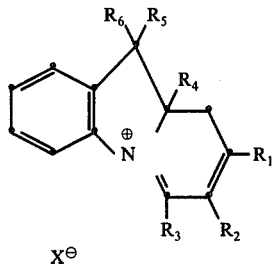

I.

where
$R_1$ and $R_3$ are, independently, lower alkyl or aryl provided at least one of them is lower alkyl;
$R_2$ is hydrogen, lower alkyl or aryl; or
$R_2$ and $R_3$, taken together, complete a fused carbocyclic ring of 5 or 6 carbon atoms;
$R_4$, $R_5$ and $R_6$ are lower alkyl; and
$X^\ominus$ is an anion; or

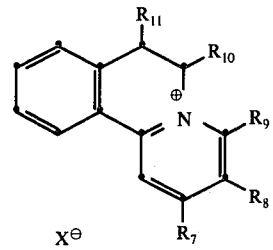

II.

where
$R_7$ and $R_9$ are, independently, lower alkyl or aryl provided at least one of them is lower alkyl;
$R_8$ is hydrogen, lower alkyl or aryl; or
$R_8$ and $R_9$, taken together, complete a fused carbocyclic ring of 5 or 6 carbon atoms or a fused ring having the structure

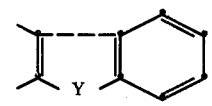

where
Y is —CH$_2$—,

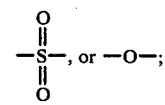

$R_{10}$ and $R_{11}$ are each hydrogen or together form a double bond or a fused benzene ring; and
$X^\ominus$ is an anion.

Structure I represents the 9,9a-dihydropyrido[1,2-a]-indolium nuclei, while structure II represents the 6,7-dihydrobenzo[a]quinolizinium nuclei when $R_{10}$ and $R_{11}$ are hydrogen and the benzo[a]quinolizinium nuclei when $R_{10}$ and $R_{11}$ have the other values given above.

These compounds can be utilized in conventional reactions to yield cyanine and merocyanine dyes. The reaction occurs at the alkyl group in the 6 or 8 position of the 9,9a-dihydropyrido[1,2-a]indolium nucleus (i.e., the alkyl group represented by $R_1$ or $R_3$) and at the alkyl group in the 2 or 4 position of the 6,7-dihydrobenzo[a]-quinolizinium nucleus or the benzo[a]quinolizinium nucleus (i.e., the alkyl groups represented by $R_7$ or $R_9$), except when Y is —CH$_2$—, in which case the reaction occurs at Y in preference to $R_7$. In some instances, when both $R_1$ and $R_3$ or $R_7$ and $R_9$ are lower alkyl, they each can react, thus leading to a trinuclear dye.

Accordingly, dyes of this invention can be represented by the structures:

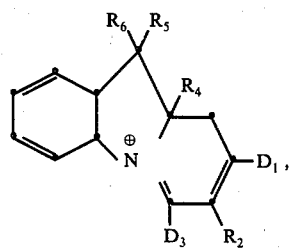

III.

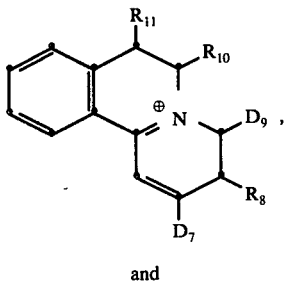

IV.

and

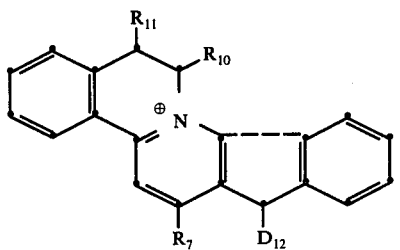

V.

where $R_2$, $R_4$, $R_5$, $R_6$, $R_{10}$ and $R_{11}$ are the same as defined above;

$D_{12}$ represents the atoms required to complete a cyanine or merocyanine dye;

$D_1$, $D_3$, $D_7$ and $D_9$ are each, independently, lower alkyl, aryl, or the atoms required to complete a cyanine or merocyanine dye, provided that at least one of $D_1$ and $D_3$ and at least one of $D_7$ and $D_9$ represents the atoms to complete a cyanine or merocyanine dye; or $R_2$ and $D_3$, taken together complete a fused carbocyclic ring of 5 or 6 carbon atoms; and $R_8$ and $D_9$, taken together complete a fused carbocyclic ring of 5 or 6 carbon atoms or a fused ring having the structure

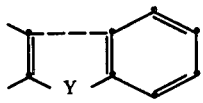

where

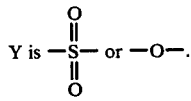

$Y$ is $-\overset{\overset{O}{\|}}{\underset{\underset{O}{\|}}{S}}-$ or $-O-$.

As used in the above structural formulae, lower alkyl refers to straight chain or branched chain alkyl groups containing 1 to 6 carbon atoms. Preferred alkyl groups are methyl and ethyl. Aryl refers to aromatic groups of the benzene series having 6 to 10 carbon atoms. A preferred aryl group is phenyl. Preferred carbocyclic rings of 5 or 6 carbon atoms, are cyclopentyl and cyclohexyl. Those skilled in the art will recognize that the above substituents can be replaced with equivalent substituents which will not adversely affect the reactivity of the intermediates of the spectral sensitizing properties of the methine dyes.

Although structural formulae III, IV and V are shown with an unsatisfied positive charge, it will be recognized that, depending upon the type of dye, this charge will be satisfied either by an associated anion as in the case of cyanine dye 1, infra, or internally in the dye molecule as in the case of zwitterionic cyanine dye 26, infra, and merocyanine dye 3, infra.

It is, of course, recognized that merocyanine dyes are capable of resonating between a zwitterionic form and an uncharged form.

The methine dyes of this invention contain a second nucleus joined to the nucleus derived from the compounds of formula I or II, above, by a methine chain. This methine chain is a chain of carbon atoms with alternating double and single bonds and forms a part of the conjugated carbon atom chain which joins the terminal hetero atoms of the dye chromophore.

As is recognized by those skilled in the art, the length of the methine chain affects the spectral absorption of the dye. The longer the methine chain, the longer the wavelength of radiation absorbed by the dye, other things being equal. The number of carbon atoms in the methine chain can vary from one to seven or greater. Shorter chain lengths, which give dyes that absorb in the visible region of the spectrum, are preferred for most uses. The number of atoms in the methine chain is such that the conjugated carbon atom chain has an even number of alternating single and double bonds. Most conventional cyanine dyes have a methine chain containing an odd number of carbon atoms; for example one, three or five carbon atoms. Most conventional merocyanine dyes have a methine chain containing an even number of carbon atoms; for example two, or four carbon atoms.

The second nucleus of the methine dyes of the invention can be any of the nuclei typically employed in cyanine or merocyanine dyes. Such nuclei are well known to those skilled in the art, as are the methods by which they can be reacted with the intermediates described above to yield cyanine or merocyanine dyes.

Representative nuclei of the type used in cyanine dyes include sensitizing nuclei such as a heterocyclic nucleus of the thiazole series (e.g., thiazole, 4-methylthiazole, 5-methylthiazole, 4-phenylthiazole, 5-phenylthiazole, 4,5-dimethylthiazole, 4,5-diphenylthiazole, 4-(2-thienyl)thiazole, etc.), those of the benzothiazole series (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-methylenedioxybenzothiazole, 5-hydroxybenzothiazole, etc.), those of the naphthothiazole series (e.g., naphtho[2,1-d]thiazole, naphtho[1,2-d]thiazole, 5-methoxynaphtho[1,2-d]thiazole, 5-ethoxynaphtho[1,2-d]thiazole, 7-methoxynaphtho[2,1-d]thiazole, 8-methoxynaphtho[1,2-d]thiazole, etc.), those of the thieno[2,3-e]benzothiazole series (e.g., 4'methoxythieno[2,3-e]benzothiazole, etc.), those of the oxazole series (e.g., 4-methyloxazole, 5-methyloxazole, 4-phenyloxazole, 4,5-diphenyloxazole, 4-ethyloxazole, 4,5-dimethyloxazole, 5-phenyloxazole, etc.), those of the benzoxazole series (e.g., benzoxazole, 5-chlorobenzoxazole, 5-phenylbenzoxazole, 5-methylbenzoxazole, 6-methylbenzoxazole, 5,6-dimethylbenzoxazole, 4,6-dimethylbenzoxazole, 5-methoxybenzoxazole, 6-methoxybenzoxazole, 5-ethoxybenzoxazole, 6-chlorobenzoxazole, 5-hydroxybenzoxazole, 6-hydroxybenzoxazole, etc.), those of the naphthoxazole series (e.g., naphth[2,1-d]oxazole, naphth[1,2-d]oxazole, etc.), those of the selenazole series (e.g., 4-methylselenazole, 4-phenylselenazole, etc.), those of the benzoselenazole series (e.g., benzoselenazole, 5-chlorobenzoselenazole, 5-methoxybenzoselenazole, 5-hydroxybenzoselenazole, tetrahydrobenzoselenazole, etc.), those of the naphthoselenazole series (e.g., naphtho[2,1-d]selenazole, naphtho[1,2-d]selenazole, etc.), those of the thiazoline series (e.g., thiazoline, 4-methylthiazoline, etc.), those of the quinoline series (e.g., 2-quinoline, 4-quinoline, 6-methoxyquinoline, 7-methylquinoline, 8-methylquinoline, etc.), those of the 1-isoquinoline series (e.g., isoquinoline, 3,4-dihydroisoquinoline, etc.,), those of the 3,3-dialkyl-3H-indole series (e.g., 3,3-dimethyl-3H-indole, 3,3,5-trimethyl-3H-indole, 3,3,7-trimethyl-3H-indole, etc.), those of the pyridine series (e.g., 2-pyridine, 4-pyridine, 3-methylpyridine, 4-methylpyridine, 5-methylpyridine, 6-methylpyridine, 3,4-dimethylpyridine, 3,5-dimethylpyridine, 3,6-dimethylpyridine, 4,5-dimethylpyridine, 4,6-dimethylpyridine, 4-chloropyridine, 5-chloropyridine, 6-chloropyridine, 3-hydroxypyridine, 4-hydroxypyridine, 5-hydroxypyridine, 6-hydroxypyridine, 3-phenylpyridine, 4-phenylpyridine, 6-phenylpyridine, etc.), those of the imidazole series (e.g., imidazole, 4-methylimidazole, 5-ethylimidazole, 4-chloroimidazole, 4,5-dichloroimidazole, 4-methoxyimidazole, 5-phenylimidazole, etc.), those of the benzimidazole series (e.g., benzimidazole, 4-methylbenzimidazole, 5-methylbenzimidazole, 6-methylbenzimidazole, 5,6-dichlorobenzimidazole, 5-chlorobenzimidazole, 5-phenylbenzimidazole, 6-phenylbenzimidazole, etc.), those of the naphthimidazole series (e.g., naphth[2,1-d]imidazole, naphth[1,2-d]imidazole, etc.), or a desensitizing nucleus, such as an imidazo[4,5-b]quinoxaline nucleus, a 5- or 6-nitrobenzothiazole nucleus, or any of the desensitizing nuclei described in Heseltine et al. U.S. Pat. No. 3,582,348 issued June 1, 1971.

Representative nuclei of the type used in merocyanine dyes include those of the 2-pyrazolin-5-one series (e.g., 3-methyl-1-phenyl-2-pyrazolin-5-one, 3-ethyl-1-phenyl-2-pyrazoliin-5-one, 1-methyl-3-phenyl-2-pyrazolin-5-one, etc.) those of the 3,4,6-triketohexahydropyrimidine or 2,6-diketo-4-thiohexahydropyrimidine series (e.g., barbituric acid or 2-thiobarbituric acid) as well as their 1-alkyl (e.g., 1-methyl, 1-ethyl, 1-n-propyl, 1-n-heptyl, etc.), or 1,3-dialkyl (e.g., 1,3-dimethyl, 1,3-diethyl, 1,3-di-n-propyl, etc., cycloalkyl such as dicyclohexyl, etc., or 1,3-diaryl (e.g., 1,3-diphenyl, 1,3-di(p-chlorophenyl), etc.), or 1-aryl (e.g. 1-phenyl, 1-p-chlorophenyl, 1-p-ethoxycarbonylphenyl, etc.), or 1-alkyl-3-aryl (e.g., 1-ethyl-3-phenyl, 1-n-heptyl-3-phenyl, etc.) derivatives, etc.; those of the rhodanine series (e.g., rhodanine, 3-ethylrhodanine, 3-propylrhodanine, 3-butylrhodanine, 3-(p-carboxyphenyl)rhodanine, 3-(p-sulfophenyl)rhodanine, etc.) those of the hydantoin series (e.g. hydantoin, 1-(p-carboxyphenyl)-3-phenylhydantoin, 1-ethyl-3-phenylhydantoin, etc.), those of the thiohydantoin series (e.g., 2-thiohydantoin, 1-p-carboxyphenyl-3-phenyl-2-thiohydantoin, 1-p-sulfophenyl-3-phenyl-2-thiohydantoin, 1-ethyl-3-phenyl-2-thiohydantoin, etc.), and those of the 2-thio-2,4-oxazolidinedione series (e.g., 2-thio-2,4-oxazolindinedione, 3-(p-sulfophenyl)-2-thio-2,4-oxazolidinedione, 3-ethyl-2-thio-2,4-oxazolidinedione, etc.).

Representative examples of dyes of the present invention include:

(1) 3'-Ethyl-4-methyl-2-benzo[a]quinolizino thiacarbocyanine salt;
(2) 3'-Ethyl-4-methyl-2-benzo[a]quinolizino oxacarbocyanine salt;
(3) 1,3,-Diethyl-5-[(4-methylbenzo[a]quinolizidin-2-ylidene) ethylidene]-2-thiobarbituric acid;
(4) 3'-Ethyl-1,2,3,4-tetrahydro-13-dibenzo[a,f]quinolizino oxacarbocyanine salt;
(5) 3'-Ethyl-2-phenyl-2-benzo[a]quinolizino oxacarbocyanine salt;
(6) 3'-Ethyl-2-phenyl-2-benzo[a]quinolizino thiacarbocyanine salt;
(7) 3-Ethyl-5-[(2-phenyl-4H-benzo[a]quinolizin-4-ylidene) ethylidene]rhodanine;
(8) 1,3-Diethyl-5-[(2-phenyl-4H-benzo[a]quinolizin-4-ylidene) ethylidene]-2-thiobarbituric acid;
(9) 3'-Ethyl-9,9a-dihydro-8,9a,10,10-tetramethyl-6-pyrido [1,2-a]indolothiacarbocyanine salt;
(10) 3'-Ethyl-9,9a-dihydro-6,9a,10,10-tetramethyl-8-pyrido [1,2-a]indolothiacarbocyanine salt;
(11) 3-Ethyl-9',9a'-dihydro-8',9a',10',10'-tetramethyloxa-6'-pyrido[1,2-a]indolocarbocyanine salt;
(12) 3-Ethyl-9',9a'-dihydro-6',9a',10',10'-tetramethyloxa-8'-pyrido[1,2-a]indolocarbocyanine salt;
(13) 3'-Ethyl-1,2,3,4,6,7-hexahydro-13-dibenzo[a,f]quinolizino thiacarbocyanine salt;
(14) 3'-Ethyl-1,2,3,4,6,7-hexahydro-13-dibenzo[a,f]quinolizino oxacarbocyanine salt;
(15) 1,3-Diethyl-5-[(1,2,3,4,6,7-hexahydro-13H-dibenzo[a,f]quinolizin-13-ylidene)ethylidene]-2-thiobarbituric acid;
(16) 3-Ethyl-5-[(1,2,3,4,6,7-hexahydro-13H-dibenzo[a,f]quinolizin-13-ylidene)ethylidene]-2-thiobarbituric acid;
(17) 7-[(3-Ethyl-2-benzothiazolinylidene)ethylidene]-13,14-dihydro-6-methyl-7H-benzo[a]indeno[1,2'-f]quinolizinium salt;
(18) 7-[(3-Ethyl-2-benzooxazolinylidene)ethylidene]-13,14-dihydro-6-methyl-7H-benzo[a]indeno[1,2'-f]quinolizinium salt;
(19) 3-Ethyl-6'-methyloxa-8'-pyrido[1,2-f]phenanthridinocarbocyanine salt;
(20) 1,3-Diethyl-5-[(6-methyl-8H-pyrido[1,2-f]phenanthridin-8-ylidene)ethylidene]-2-thiobarbituric acid;
(21) 6,8-Bis(3-ethylbenzothiazolinylidene-propenyl)-pyrido [1,2-f]phenanthridinium salt;
(22) 3'-Ethyl-6-methyl-8-pyrido[1,2-f]phenanthridino thiacarbocyanine salt;
(23) 3'-Ethyl-8-phenyl-6-pyrido[1,2-f]phenanthridino thiacarbocyanine salt;
(24) 3'-Ethyl-8'-phenyloxa-6'-pyrido[1,2-f]phenanthridino carbocyanine salt;
(25) 1,3-Diethyl-5-[(8-phenyl-6H-pyrido[1,2-f]phenanthridin-6-ylidene)ethylidene]-2-thiobarbituric acid;
(26) Anhydro-3'-(3-sulfopropyl)-1,2,3,4,-tetrahydro-5'-methoxy-13-dibenzo[a,f]quinolizinooxacarbocyanine hydroxide; and
(27) 3'-Ethyl-13,14-dihydro-7,7-dioxo-6-benzo[a]benzothieno [3,2-f]quinolizino thiacarbocyanine salt.

The novel quaternary salts used in preparing the dyes of this invention can be formed by reacting a ketone having the following general structure:

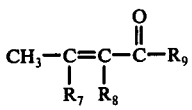

where
R$_7$, R$_8$ and R$_9$ are as defined above, with the appropriate protonated nitrogen containing heterocyclic ring having the general structure:

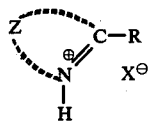

(B)

wherein Z represents the atoms necessary to complete a heterocyclic nucleus, R is hydrogen or lower alkyl and X$^\ominus$ is an acid anion. While the mechanism of the reaction is not known for certain, it is believed that the ketone (A) adds to the double bond of (B) as follows:

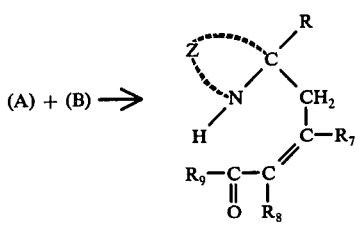

(C)

The intermediate (C) then undergoes ring closure between the carbonyl group and the nitrogen atom to form a heterocyclic 6-membered ring containing two double bonds as illustrated by the following formula:

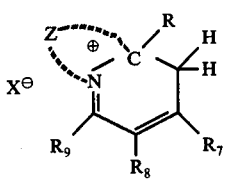

(D)

If R on compound (B) is alkyl the reaction sequence ends with compound (D). However, if R is a hydrogen atom, aromatization occurs to yield compound (E).

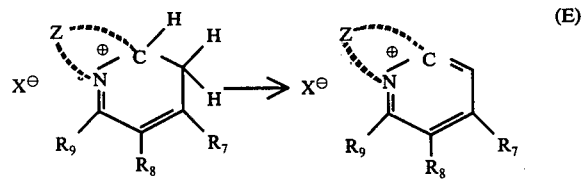

(E)

The dyes of this invention spectrally sensitize photographic silver halide emulsions by extending the region of the spectrum to which the emulsion exhibits a photographic response. Photographic silver halide emulsions which may be so sensitized can be negative working, reversal, or direct positive emulsions comprised of, for example, silver chloride, silver bromide, silver bromoiodide, silver chlorobromide, silver chloroiodide, silver chlorobromoidide crystals or mixtures of such crystals. The emulsions can be coarse or fine grain emulsions and can be prepared by a variety of techniques, e.g., single jet emulsions such as those described in Trivelli and Smith, The Photographic Journal, Vol. LXXIX, May 1939 (pp. 330–338), double jet emulsions such as Lippmann emulsions, ammoniacal emulsions, thiocyanate or thioether ripened emulsions such as those described in Nietz et al. U.S. Pat. No. 2,222,264 issued November 19, 1940; Illingsworth U.S. Pat. No. 3,320,069 issued May 17, 1967 and McBride U.S. Pat. No. 3,271,157 issued Sept. 6, 1966. The silver halide emulsions can form latent images predominantly on the surface of the silver halide grains, or predominantly on the interior of the silver halide grains such as those described in Davey et al U.S. Pat. No. 2,592,250 issued May 8, 1952; Porter et al U.S. Pat. No. 3,206,313 issued Sept. 14, 1965; Berriman U.S. Pat. No. 3,367,778 issued Feb. 6, 1968 and Bacon et al. U.S. Pat. No. 3,447,927 issued June 3, 1969. If desired, mixtures of such surface and internal image-forming emulsions can be made, such being described in Luckey et al. U.S. Pat. No. 2,996,382 issued Aug. 15, 1961. Silver halide emulsions can be regular grain emulsions such as the type described in Klein and Moisar, J. Phot. Sci., Vol. 12, No. 5, Sept./Oct., 1964, pp. 242–251. Negative type emulsions can be made, as well as direct positive emulsions as described in Leermakers U.S. Pat. No. 2,184,013 issued Dec. 19, 1939; Kendall et al, U.S. Pat. No. 2,541,472 issued Feb. 13, 1951; Schouwenaars British Pat. No. 723,019 issued Feb. 2, 1955; Illingsworth et al. French Pat. No. 1,520,821 issued Mar. 4, 1968; Illingsworth U.S. Pat. No. 3,501,307 issued Mar. 17, 1970; Ives U.S. Pat. No. 2,563,785 issued Aug. 7, 1951; Knott et al. U.S. Pat. No. 2,456,953 issued Dec. 21, 1948 and Land U.S. Pat. No. 2,861,885 issued Nov. 25, 1958.

The silver halide emulsions can be unwashed or washed to remove soluble salts after precipitation of the silver halide. In the latter case, the soluble salts can be removed by chill-setting and leaching or the emulsion can be coagulation washed, e.g., by the procedures described in Hewitson et al. U.S. Pat. No. 2,618,556 issued Nov. 18, 1952; Yutzy et al. U.S. Pat. No. 2,614,928 issued Oct. 21, 1952; Yackel U.S. Pat. No. 2,565,418 issued Aug. 21, 1951; Hart et al. U.S. Pat. No. 3,241,969 issued Mar. 22, 1966 and Waller et al. U.S. Pat. No. 2,489,341 issued Nov. 29, 1949.

The dyes of this invention are advantageously incorporated in the washed, finished emulsion and should be uniformly distributed throughout the emulsion. The dyes can be added from solutions in appropriate solvents which are compatible with the emulsion and which are substantially free from deleterious effects on the light-sensitive materials.

The types of silver halide emulsions that can be sensitized with the new dyes of this invention include those prepared with hydrophilic colloids that are known to be satisfactory vehicles for dispersed silver halides, for example, emulsions comprising both naturally-occurring substances such as proteins, for example, gelatin, gelatin derivatives, cellulose derivatives, polysaccharides such as detran, gum arabic and the like; and synthetic polymeric substances such as water-soluble polyvinyl compounds like poly(vinylpyrrolidone), acryamide polymers and the like. The photographic emulsions can also contain alone or in combination with hydrophilic, water-permeable colloids, other synthetic polymeric vehicle compounds such as dispersed vinyl compounds such as in latex form and particularly those which increase the dimensional stability of the photographic materials. Typical synthetic polymers include those described in Nottorf U.S. Pat. No. 3,142,568 issued July 28, 1964; White U.S. Pat. No. 3,193,386 issued July 6, 1965; Houck et al. U.S. Pat. No. 3,062,674 issued Nov. 6, 1962; Houck et al. U.S. Pat. No. 3,220,844 issued Nov. 30, 1965; Ream et al. U.S. Pat. No. 3,287,289 issued Nov. 22, 1966; and Dykstra U.S. Pat. No. 3,411,911 issued Nov. 19, 1968. Other materials include water-insoluble polymers of alkyl acrylates and methacrylates, acrylic acid, sulfoalkyl acrylates or methacrylates, those which have cross-linking sites which facilitate hardening or curing as described in Smith U.S. Pat. No. 3,488,708 issued Jan. 6, 1970, and those having recurring sulfobetaine units as described in Dykstra Canadian Pat. No. 774,054.

The concentration of the new dyes in the emulsion can vary widely, e.g., from about 25 to 1000 mg. per mole of silver in flowable emulsion. The specific concentration will vary according to the type of light-sensitive material in the emulsion and the effects desired. The suitable and most economical concentration for a given emulsion will be apparent to those skilled in the art upon making the tests and observations customarily used in the art of emulsion making.

To prepare a gelatin-silver halide emulsion sensitized with one of the dyes of this invention, the following procedure is satisfactory. A quantity of the dye is dissolved in a suitable solvent and a volume of this solution containing from 25 to 1000 mg. of dye per mole of silver is slowly added to the gelatin-silver halide emulsion. With most of the dyes, 50 to 500 mg. of dye per mole of silver suffices to produce the maximum sensitizing effect with the ordinary gelatin-silver bromide (including bromoiodide and chlorobromide) emulsions. With fine grain emulsions, which include most of the ordinarily employed gelatin-silver chloride emulsions, somewhat larger concentrations of dye may be necessary to obtain the optimum sensitizing effect. While this procedure has dealt with emulsions comprising gelatin, it will be appreciated that these remarks apply generally to any emulsion wherein all or part of the gelatin is substituted by another suitable hydrophilic colloid as mentioned above. Binderless light-sensitive silver halide grains can also be spectrally sensitized with the dyes of this invention.

Photographic silver halide emulsions spectrally sensitized in accordance with this invention can contain chemical sensitizers, stabilizers, antifoggants, development modifiers, hardeners, vehicles, plasticizers, coating aids, other spectral sensitizing dyes, etc., and can be coated on supports, such as those described and referred to in *Product Licensing Index*, Vol. 92, December, 1971, pubilication 9232, pages 107–110. Such emulsions are useful in photographic elements which may contain developing agents, antistatic layers, matting agents, brighteners, absorbing and filter dyes, color-forming couplers, etc., described and referred to in the above-mentioned *Product Licensing Index*, pages 108–110. Processing of photographic silver halide grains spectrally sensitized in accordance with this invention can be accomplished by the methods described and referred to on page 110 of the above-identified *Product Licensing Index*.

Photographic elements incorporating the sensitized silver halide emulsions of this invention can be made by coating the emulsions on any suitable support, of which a wide variety are known in the art. Typical supports include cellulose nitrate film, cellulose acetate film, poly(vinyl acetal) film, poly(ethylene terephthalate) film, polycarbonate film and related films or resinous materials, as well as glass, paper, metal and the like. Tpically, a flexible support is employed, especially a paper support, which can be partially acetylated or coated with baryta and/or an alpha-olfin polymer, particularly a polymer of an alpha-olefin containing 2 to 10 carbon atoms such as polyethylene, polypropylene, ethylenebutene copolymers and the like. Photographic elements incorporating this invention can be coated by the procedures described and referred to in page 109 of the above-identified *Product Licensing Index*, Vol. 92, December 1971.

The following examples are included for a further understanding of the invention. Examples 1–16 illustrate the production of the intermediate quaternary salts. Examples 17–33 illustrate the formation of particular dyes using the quaternary salts of this invention. All temperatures are in degrees centigrade.

EXAMPLE 1

2,4-Dimethylbenzo[a]quinolizinium perchlorate

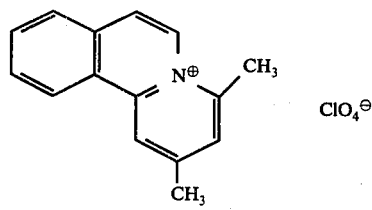

Isoquinolinium perchlorate (10 g) and mesityl oxide (20 ml) were heated together at 125°–130° for 2 days. Ethanol (10 ml) was added and the mixture chilled to 0°. The product was filtered off and recrystallized from acetonitrile. Yield 4.5 g, mp 278° C.

Anal. Calcd. for $C_{15}H_{14}ClNO_4$: C, 58.5; H, 4.6; N, 4.6. Found: C, 58.8, H, 4.5; N, 4.6%.

EXAMPLE 2

9,9a-Dihydro-6,8,9a,10,10-pentamethylpyrido[1,2-a]indolium perchlorate

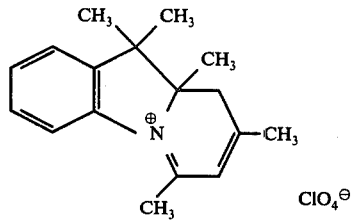

2,3,3-Trimethyl-3H-indolium perchlorate (10 g) was refluxed gently in mesityl oxide (20 ml) for 5 hours. The reaction mixture was evaporated to dryness and dissolved in ethanol (15 ml). The solution was chilled overnight and the product removed by filtration. After recrystallization from ethanol the product melted at 190° C and weighed 2.2 g.

Anal. Calcd. for $C_{17}H_{20}ClNO_4$: C, 60.1; H, 6.5; N, 4.1. Found: C, 60.1; H, 6.5; N, 4.4%.

EXAMPLE 3

4-Methyl-2-phenylbenzo[a]quinolizinium perchlorate

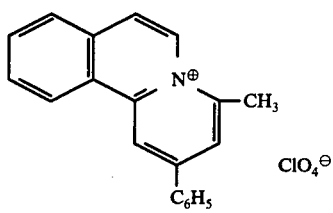

Isoquinolinium perchlorate (10 g) and 4-phenylpent-3-ene-2-one (15 g) were heated together at 140°–150° C for 2 days. The cooled melt was treated with ethanol and filtered. The product was recrystallized from acetonitrile. Yield 5 g m.p. >300°.

Anal. Calcd. for $C_{20}H_{16}ClNO_4$: C, 65.7; H, 4.4; N, 3.8. Found: C, 65.8; H, 4.6; N. 3.7%.

EXAMPLE 4

1,2,3,4-Tetrahydro-13-methyl dibenzo[a,f]quinolizinium perchlorate

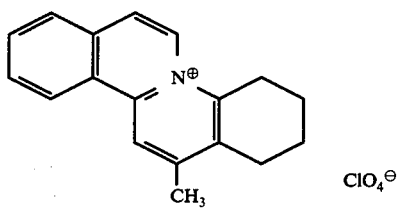

Isoquinolinium perchlorate (5 g) and 2-isopropylidenecyclohexanone (8 g) were heated together at 140° C for 3 days. The cooled reaction mixture was diluted with ethanol and filtered. The product after recrystallization from acetonitrile or methanol melted at 277° C. Yield 2 g.

Anal. Calcd. for $C_{18}H_{18}ClNO_4$: C, 62.1; H, 5.2; N, 4.0. Found: C, 61.9; H, 5.3; N, 4.0%.

EXAMPLE 5

2-Methyl-4-phenylbenzo[a]quinolizinium perchlorate

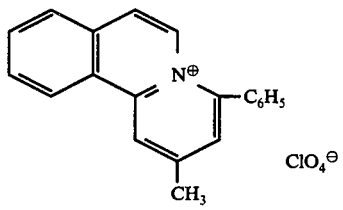

Isoquinolinium perchlorate (0.9 g) and 3-methyl-1-phenylpent-2-ene-1-one (1.1 g) were heated together at 125° for 3 days. Ethanol was added to the cooled mixture and the product filtered off. After recrystallization from ethanol the product melted at 300° C. Yield 0.3 g.

EXAMPLE 6

1,2,3,4,6,6a-Hexahydro-5,6a,7,7-tetramethylindolo[1,2-a] quinolinium perchlorate

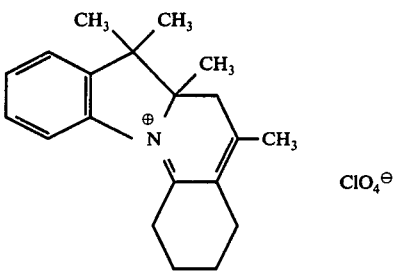

2,3,3-Trimethyl-3H-indolium perchlorate (0.5 g) and 2-isopropylidene cyclohexanone (0.75 g) were heated at 150° C for 2½ hours. The reaction mixture was diluted with ethanol, chilled to 0° and filtered. The product was recrystallized from ethanol. m.p. 228°–230°.

Anal. Calcd. for $C_{20}H_{26}NO_4$: C, 63.2; H, 6.9; N, 3.7. Found: C, 62.9; H 6.8; N, 3.5%.

EXAMPLE 7

1,2,3,4,6,7-Hexahydro-13-methyldibenzo[a,f]quinolizinium perchlorate

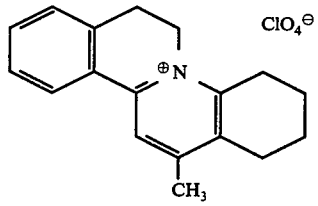

3,4-Dihydroisoquinolinium perchlorate (4.6 g) and 2-isopropylidenecyclohexanone (3 g) were dissolved in dimethylforamide (12 ml) and refluxed for 12 hours. The reaction mixture was cooled, diluted with ethanol, and filtered. The product was purified by recrystallization from methanol. Yield 3 g; m.p. 205°.

Analysis: Calcd for $C_{18}H_{20}ClNO_4$: C, 61.8; H, 5.8; N, 4.0; Found: C, 61.5; H, 5.7; N, 3.9.

EXAMPLE 8

13,14-Dihydro-6-methyl-7H-benzo[a]indeno[1,2-f]quinolizinium perchlorate

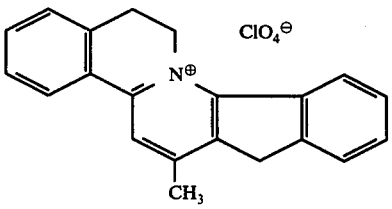

3,4-Dihydroisoquinolinium perchlorate (2 g) and 2-isopropylidene-indan-1-one (2 g) were heated together at 150° for 2 hours. The reaction mixture was cooled and diluted with methanol. The product was collected by filtration and recrystallized from methanol. Yield 2.6 g, m.p. 247°.

Anal. Calcd. for $C_{21}H_{18}ClNO_4$: C, 65.5; H, 4.7; N, 3.7; Found: C, 65.4; H, 4.9; N, 3.6.

EXAMPLE 9

6,7-Dihydro-2,4-dimethylbenzo[a]quinolizinium perchlorate

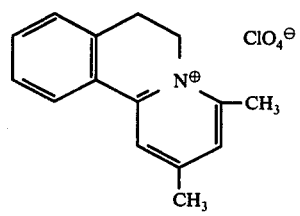

3,4-Dihydroisoquinolinium perchlorate (5 g) and mesityloxide (10 ml) were heated together at 150° for 16 hours. The reaction mixture was diluted with methanol and chilled. The product was collected and recrystallized from methanol. Yield 3 g, m.p. 176°–8°.

Anal. Calcd. for $C_{15}H_{16}ClNO_4$: C, 58.1; H, 5.2; N, 4.5; Found: C, 57.8; H, 5.1; N, 4.6.

EXAMPLE 10

6,8-Dimethylpyrido[1,2-f]phenanthridinium perchlorate

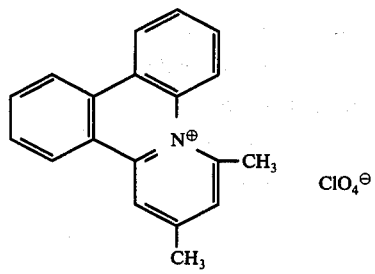

This compound was prepared by the method described in Example 9 except that phenanthridinium perchlorate was used in place of 3,4-dihydroisoquinolinium perchlorate. The product was recrystallized from acetonitrile. Yield 70%, m.p. 231°–2°.

Analysis Calcd. for $C_{19}H_{16}ClNO_4$: C, 63.8; H, 4.5; N, 3.9; Found: C, 63.6; H, 4.2; N, 3.5.

EXAMPLE 11

6-Methyl-8-phenylpyrido[1,2-f]phenanthridinium perchlorate

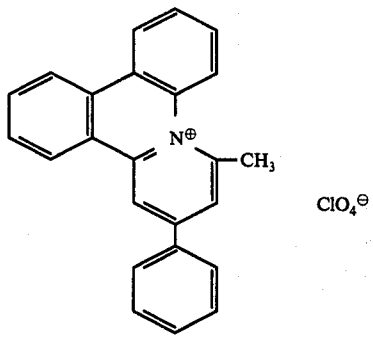

Phenanthridinium perchlorate (2 g) and 4-phenyl-pent-3-ene-2-one (4 g) were heated together at 150° for 16 hours. The reaction mixture was cooled and diluted with methanol. The product was isolated by filtration and recrystallized from acetonitrile. Yield 1.5 g, m.p. 252°–3°.

Anal. Calcd. for $C_{24}H_{18}ClNO_4$: C, 68.7; H, 4.3; N, 3.3; Found: C, 68.6; H, 3.9; N, 3.2.

EXAMPLE 12

13,14-Dihydro-6-methyl-7,7-dioxobenzo[a]benzothieno[3,2-f]-quinolizinium perchlorate

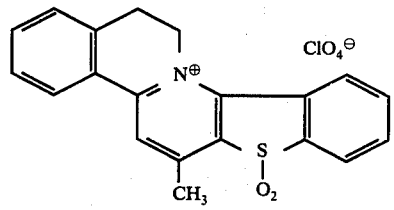

3,4-Dihydroisoquinolinium perchlorate (1.2 g) and 2-isopropylidenebenzothien-3-one-1,1-dioxide (2 g) were heated together at 150° for 16 hours. The reaction mixture was triturated with hot methanol and filtered. The product was purified by recrystallization from acetonitrile. Yield 0.6 g, m.p. > 330°.

Anal. Calcd. for $C_{20}H_{16}ClNO_6$: C, 55.4; H, 3.8; N, 3.2; Found: C, 55.1; H, 4.2; N, 2.9.

EXAMPLE 13

12-Methylbenzo[a]cyclopenta[f]quinolizinium perchlorate

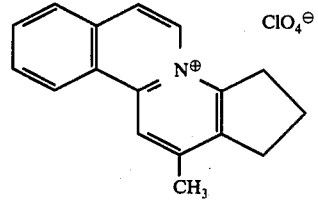

Isoquinolinium perchlorate (2.3 g) and 2-isopropylidene cyclopentanone (1.5 g) in dimethylformamide (5 ml) were refluxed for 18 hours. The reaction mixture was cooled, diluted with methanol and filtered. Purification was effected by recrystallization from acetonitrile (norite). Yield 1.5 g, m.p. > 300°, Anal. Calcd. for $C_{17}H_{16}ClNO_4$: C, 61.2; H, 4.8; N, 4.2; Found: C, 61.2; H, 4.9; N, 4.2.

EXAMPLE 14

13,14-Dihydro-6-methylbenzo[a]benzofuro[3,2-f]quinolizinium perchlorate

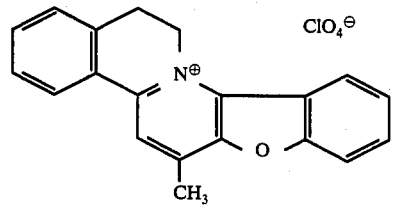

This compound was prepared by the method described in Example 12 except that 2-isopropylidene-2H-benzofuran-3-one was used in place of 2-isopropylidenebenzothien-3-one-1,1-dioxide. The product was purified by recrystallization from acetonitrile. m.p. 272°.

Anal. Calcd. for $C_{20}H_{16}ClNO_5$: C, 62.2; H, 4.2; N, 3.6; Found: C, 61.8, H, 4.6; N, 3.3.

EXAMPLE 15

3'Ethyl-4-methyl-2-benzo[a]quinolizino oxacarbocyanine perchlorate

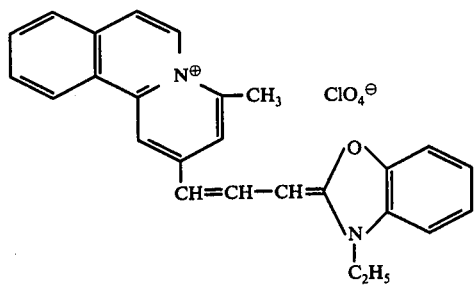

2,4-Dimethylbenzo[a]quinolizinium perchlorate (0.6 g) and 2-(2-acetanilidovinyl)-3-ethylbenzoxazolium perchlorate (0.8 g) were dissolved in acetonitrile and triethylamine was added. After stirring for 5 hours at room temperature, the precipitated dye was filtered off and recrystallized from acetonitrile. m.p. 278°. Yield 0.4 g, 42% $\lambda_{max}^{CH_3CN}$ 560 nm.

EXAMPLE 16

3'-Ethyl-1,2,3,4-tetrahydro-13-dibenzo[a,f]quinolizino oxacarbocyanine perchlorate

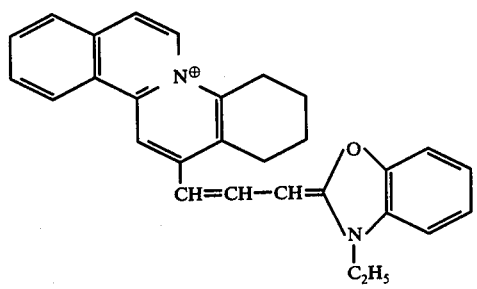

1,2,3,4-Tetrahydro-13-methyldibenzo[a,f]quinolizinium perchlorate (0.66 g) and 2-(2-acetanilidovinyl)-3-ethylbenzoxazolium perchlorate (0.77 g) were dissolved in acetonitrile and triethylamine added. After being stirred overnight the precipitated dye was filtered off and recrystallized from methanol. Yield 0.5 g 51% m.p. 248°–250° C. $\lambda_{max}^{CH_3CN}$ 564 nm.

EXAMPLE 17

3'-Ethyl-2-phenyl-2-benzo[a]quinolizino oxacarbocyanine perchlorate

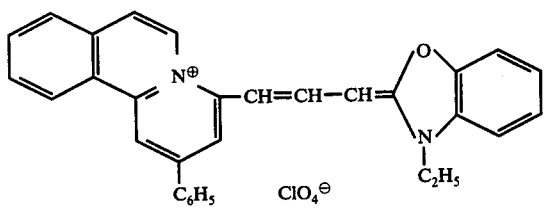

This dye was prepared by the method described in Example 16 except that 4-methyl-2-phenylbenzo[a]-quinolizinium perchlorate was used in place of the dibenzo[a,f]quinolizinium derivative. After recrystallization from methanol the dye melted at 241° C. Yield 5%. $\lambda_{max}^{CH_3CN}$ 562 nm.

EXAMPLE 18

3'-Ethyl-1,2,3,4,6,7-hexahydro-13-dibenzo[a,f]quinolizinoxacarbocyanine perchlorate

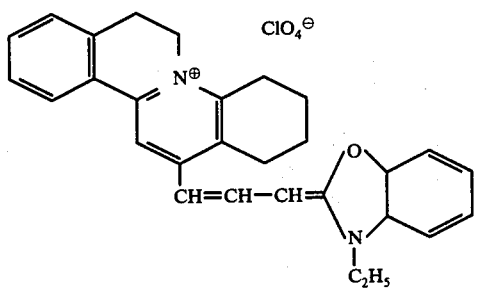

1,2,3,4,6,7-Hexahydro-13-methyldibenzo[a,f]quinolizinium perchlorate (0.7 g) and 2-(2-acetanilidovinyl)-3-ethylbenzoxazolium perchlorate (0.86 g) were stirred in acetonitrile in the presence of triethylamine. The dye precipitated from solution and was collected by filtration and purified by recrystallization from acetonitrile. Yield 0.14 g (13%), m.p. 288°, $\lambda_{max}$ in acetonitrile 532 nm, $\epsilon = 9.0 \times 10^4$.

EXAMPLE 19

7[(3-Ethyl-2-benzoxazolinylidene)ethylidene]-13,14-dihydro-6-methyl-7H-benzo[a]indeno[1,2-f]quinolizinium perchlorate

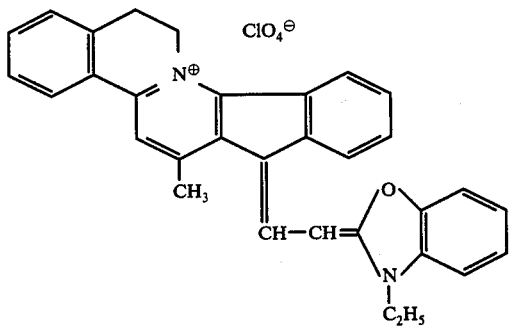

13,14-Dihydro-6-methyl-7H-benzo[a]indeno[1,2-f]quinolizinium perchlorate (0.38 g) and 2-(2-acetanilidovinyl)-3-ethylbenzoxazolium perchlorate (0.43 g) were stirred in acetonitrile in the presence of triethylamine. The dye which separated from solution was collected and recrystallized from acetonitrile. Yield 18%, m.p. 277°, $\lambda_{max}$ in acetonitrile 508 nm, $\epsilon = 10.1 \times 10^4$.

EXAMPLE 20

3-Ethyl-6'-methyloxa-8'-pyrido[1,2-f]phenanthridinocarbocyanine perchlorate

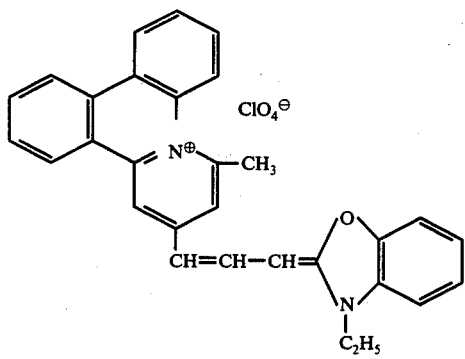

6,8-Dimethylpyrido[1,2-f]phenanthridinium perchlorate (0.76 g) and 2-(2-acetanilidovinyl)-3-ethylbenzoxazolium perchlorate (0.82 g) were stirred in acetonitrile in the presence of triethylamine overnight. The reaction mixture was evaporated to dryness and chromatographed on silica gel. The dye was recrystallized from methanol. Yield 0.2 g (20%), m.p. 217°, $\lambda_{max}$ in acetonitrile 589 nm, $\epsilon = 11.8 \times 10^4$.

EXAMPLE 21

3-Ethyl-8'-phenyloxa-6'-pyrido[1,2-f]phenanthridinocarbocyanine perchlorate

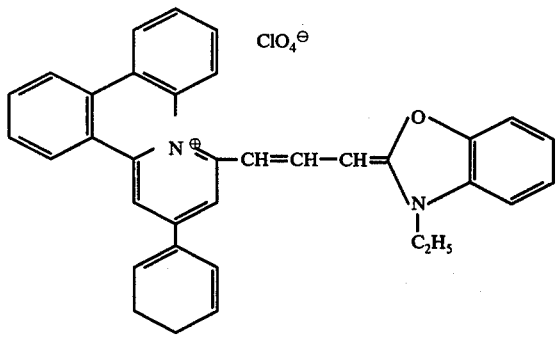

This dye was prepared by the method of Example 18 except that 6-methyl-8-phenylpyrido[1,2-f]phenanthridinium perchlorate was used in place of the quinolizinium derivative. Yield 51%, m.p. 193°–197° $\lambda_{max}$ in acetonitrile 620 nm, $\epsilon = 4.7 \times 10^4$, 465 nm, $\epsilon = 1.54 \times 10^4$.

EXAMPLE 22

A.
3-Ethyl-9',9a'-dihydro-8',9a',10',10'-tetramethyloxa-6'-pyrido[1,2-a]indolocarbocyanine perchlorate

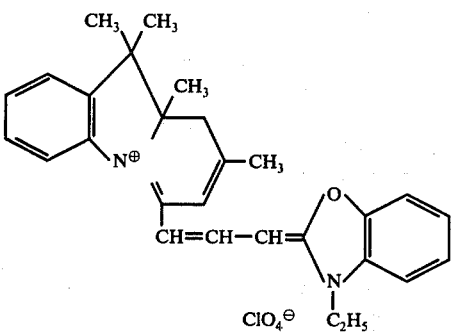

9,9a-Dihydro-6,8,10.10-tetramethylpyrido[1,2-a]indolium perchlorate (2 g) and 2-[2-acetanilido vinyl]-3-ethylbenzoxazolium perchlorate (2.5 g) were dissolved in acetonitrile and triethylamine added. After 12 hours at room temperature the reaction mixture was evaporated to dryness and chromatographed on silica gel. The first dye eluted from the column was recrystallized from ethanol. $\lambda_{max}^{CH_3CN}$ 533 nm. Yield 29% m.p. 223° C.

B.
3-Ethyl-9',9a'-dihydro-6',9a',10',10'-tetramethyloxa-8'-pyrido[1,2-a]indolocarbocyanine perchlorate

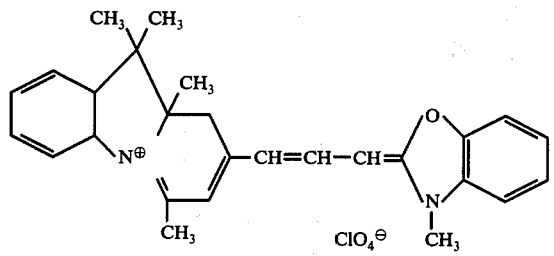

This dye was eluted from the column after the first one and was recrystallized from ethanol. $\lambda_{max}^{CH_3CN}$ 624 nm. Yield 7% m.p. 245° C.

Thiacarbocyanine dyes corresponding to the dyes in Examples 15 through 22 can be obtained by using 2-(2-acetanilidovinyl)-3-ethylbenzothiazolium perchlorate in place of 2-(2-acetanilidovinyl)-3-ethylbenzoxazolium perchlorate.

EXAMPLE 23

3-Ethyl-5-[(2-phenyl-4H-benzo[a]quinolizin-4-ylidene)ethylidene]rhodanine

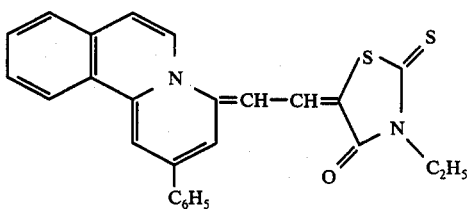

4-Methyl-2-phenylbenzo[a]quinolizinium perchlorate (0.36 g) and 5-acetanilidomethylene-3-ethyl rhodanine (0.3 g) were dissolved in acetonitrile and tetramethylguanidine (0.11 g) added. After being stirred for two hours the precipitated dye was filtered off and recrystallized from pyridine. Yield 45% m.p. 289° C $\lambda_{max}^{pyridine}$ 625 nm.

EXAMPLE 24

1,3-Diethyl-5-[(2-phenyl-4H-benzo[a]quinolizin-4-ylidene) ethylidene]-2-thiobarbituric acid.

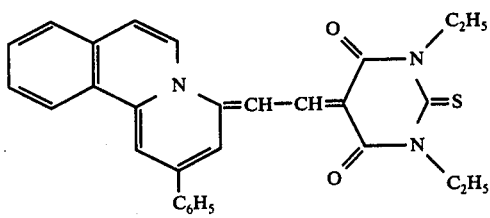

This dye was prepared by the method described in Example 23 except that 5-anilinomethylene-1,3-diethyl-2-thiobarbituric acid was used in place of the rhodanine derivative.

The dye after recrystallization from dimethylformamide melted at > 330° C. $\lambda_{max}^{pyridine}$ 555 nm. Yield 42%.

EXAMPLE 25

1,3-Diethyl-5-[(4-methylbenzo[a]quinolizindin-2-ylidene) ethylidene]-2-thiobarbituric acid

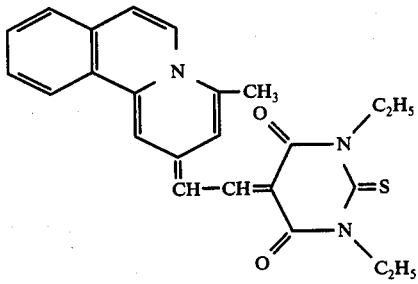

2,4-Dimethylbenzo[a]quinolizidinium perchlorate (0.9 g) and 5-anilinomethylene-1,3-diethyl-2-thiobarbituric acid (0.9 g) were dissolved in acetonitrile and treated with tetramethylguanidine (0.33 g). After being stirred at room temperature for 2 hours the dye was filtered off and recrystallized from dimethylformamide. $\lambda_{max}^{pyridine}$ 553 nm. Yield 0.6 g m.p. 323°.

EXAMPLE 26

3'-Ethyl-13,14-dihydro-7,7-dioxo-6-benzo[a]benzothieno [3,2-f]-quinolizinothiacarbocyanine perchlorate

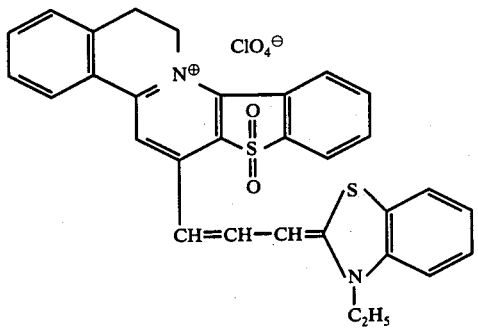

This dye was prepared by the method described in Example 18 except that 13,14-dihydro-6-methyl-7,7-dioxobenzo[a]benzothieno[3,2-f]quinolizinium perchlorate was used in place of the other quinolizinium salt and 2-(2-acetanilidovinyl)-3-ethyl-benzothiazolium perchlorate was used in place of the corresponding oxazolium salt. It was recrystallized from acetonitrile. Yield 65%, m.p. 240°–244°, $\lambda_{max}$ in acetonitrile 623 nm, $\epsilon = 9.8 \times 10^4$.

EXAMPLE 27

Anhydro-3'-(3-sulfopropyl)-1,2,3,4-tetrahydro-5'-methoxy-13-dibenzo[a,f]quinolizinooxacarbocyanine hydroxide

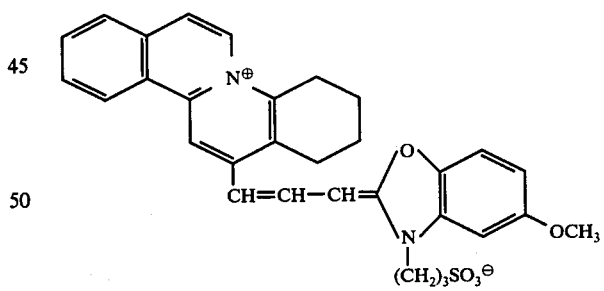

1,2,3,4-Tetrahydro-13-methyldibenzo[a,f]quinolizinium perchlorate (0.35 g) and anhydro-2-(2-anilinovinyl)-5-methoxy-3-(3-sulfopropyl)-benzoxazolium hydroxide were dissolved in a mixture of dimethylformamide (5 ml) and acetic anhydride (1 ml) and heated in the presence of triethylamine until dye formation appeared to be complete. The product was isolated by filtration and purified by recrystallization from dimethylformamide. m.p. >300°, $\lambda_{max}$ in pyridine/methanol 580 nm, $\epsilon = 8.8 \times 10^4$.

EXAMPLE 28

6,8-Bis(3-ethylbenzothiazolinylidenepropenyl)-pyrido[1,2-f]-phenanthridinium perchlorate

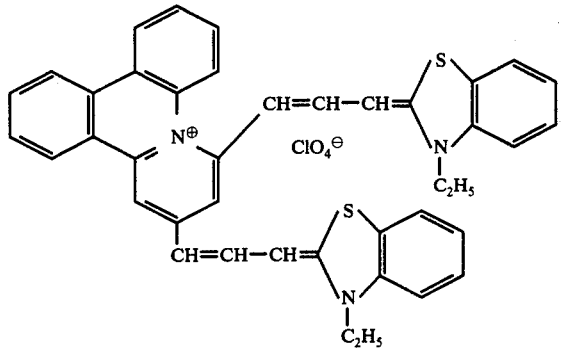

6,8-Dimethylpyrido[1,2-f]phenanthridinium perchlorate (0.76 g) and 2-(2-acetanilidovinyl)-3-ethylbenzothiozolium perchlorate (0.86 g) were stirred in acetonitrile in the presence of triethylamine overnight. The dye which separated was collected and recrystallized from acetonitrile. m.p. 205°-10°, $\lambda_{max}$ in acetonitrile 685 nm, $\epsilon = 8.1 \times 10^4$, 575 nm, $\epsilon = 6.4 \times 10^4$.

The above reaction mixture after removal of the bis dye was evaporated to dryness and chromatographed on silica gel to yield a second dye.

3'-Ethyl-6-methyl-8-pyrido[1,2-f]phenanthridinothiacarbocyanine perchlorate.

EXAMPLE 29

1,3-Diethyl-5-[(1,2,3,4,6,7-hexahydro-13H-dibenzo[a,f-]quinolizin-13-ylidene)ethylidene]-2-thiobarbituric acid

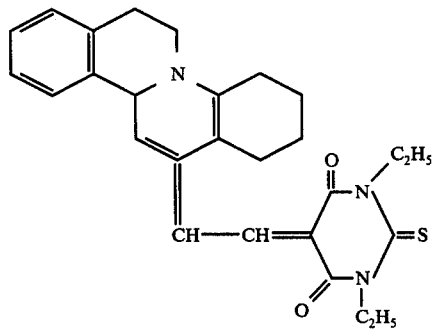

1,2,3,4,6,7-Hexahydro-13-methyldibenzo[a,f-]quinolizinium perchlorate (0.7 g) and 5-anilinomethylene-1,3-diethyl-2-thiobarbituric acid (0.6 g) were dissolved in acetonitrile and tetramethylguanidine (0.22 g) was added. The precipitated dye was collected by filtration and recyrstallized from dimethylformamide. Yield 0.4 g (44%), m.p. 320°, $\lambda_{max}$ in pyridine 522 nm, $\epsilon = 8.2 \times 10^4$.

EXAMPLE 30

1,3-Diethyl-5-[6-methyl-8H-pyrido[1,2-f]phenanthridin-8-ylidene)-ethylidene]-2-thiobarbituric acid

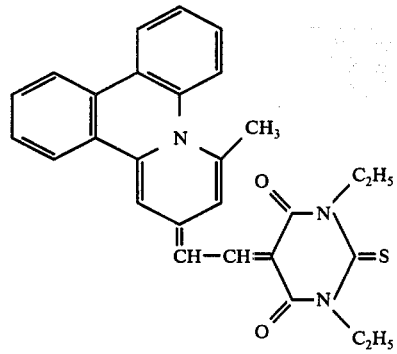

This compound was prepared by the method given in Example 29 except that 6,8-dimethylpyrido[1,2-f]phenanthridinium perchlorate was used in place of the quinolizinium derivative. It was recrystallized from dimethylformamide. m.p. 285°, $\lambda_{max}$ in pyridine 580 nm, $\epsilon = 10.4 \times 10^4$.

EXAMPLE 31

1,3-Diethyl-5-[(8-phenyl-6H-pyrido[1,2-f]phenanthridin-6-ylidene)ethylidene]-2-thiobarbituric acid

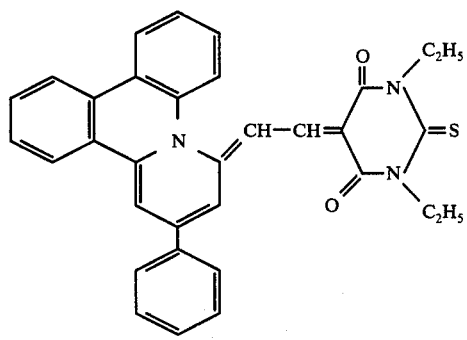

This dye was prepared by the method of Example 29 except that 6-methyl-8-phenylpyrido[1,2-f]phenanthridinium perchlorate was used in place of the quinolizinium derivative. It was recrystallized from dimethyl formamide. Yield 28%, m.p. 291°, $\lambda_{max}$ in pyridine 610 nm, $\epsilon = 3.3 \times 10^4$, 457 nm, $\epsilon = 1.28 \times 10^4$.

Dyes similar to those in Examples 29-31 can be produced by substituting 5-anilinomethylene-3-ethyl-2-thiobarbituric acid in place of the 5-anilinomethylene-1,3-diethyl-2-thiobarbituric acid.

EXAMPLE 32

Dyes prepared by the methods of the above examples were tested in a 0.2 μm sulfur-and gold-sensitized, cubic-grained silver bromoiodide gelatin emulsion containing 2.5% iodide. The dyes were added to separate portions of the emulsion at the concentrations indicated and coated at 1.1 g/m² on a cellulose acetate support. A sample of each coating was exposed to a tungsten light source in an Eastman 1B Sensitometer through a wedge spectrograph and through a continuous step wedge, using a Wratten 16 filter (minus blue). The coatings were developed in a Kodak Versamat ® roller transport processor for 80 sec. at 23° C. in an Elon (Trademark for N-methyl-p-aminophenolsulfate)hydroquinone developer.

Results for the dyes prepared in accordance with the number of the example listed are tabulated below.

TABLE 1

| Dye Example Number | Dye Conc. × 10⁻⁴ Moles/ Mole Ag | Rel. Speed 365 nm line | Rel. Speed Minus Blue | Fog | Sens. Max (nm) | Sens. Range (nm) |
|---|---|---|---|---|---|---|
| Control (1)* | — | 100 | — | .06 | — | 390–490 |
| Control (2)** | 6.0 | — | 100 | .06 | 540 | 380–500 |
| 15 | 2.0 | 246 | 219 | .07 | 605 | 500–680 |
| 16 | 6.0 | 234 | 550 | .08 | 615 | 490–680 |
| 17 | 2.0 | 234 | 174 | .06 | 625 | 520–700 |
| 22A | 6.0 | 151 | 16 | .07 | 560 | 500–600 |
| 22B | 2.0 | 195 | 22 | .06 | 660 | 620–700 |
| 23 | 8.0 | 148 | 27 | .06 | 630 | 540–680 |
| 24 | 6.0 | 200 | 48 | .06 | 560 | 490–620 |
| 25 | 6.0 | 282 | 200 | .07 | 555 | 390–620 |
| 29 | 8.0 | 331 | 80 | .07 | 525 | 390–580 |
| 27 | 2.0 | 282 | 229 | .04 | 610 | 500–680 |

*Undyed Emulsion
**Emulsion containing 3-Carboxymethyl-5-[(3-methyl-2-thiazolidinylidene)-1-methylethylidene] rhodanine

EXAMPLE 33

Dyes prepared by the above methods were tested in a 0.2 μm sulfur and gold, monodispersed gelatino silver bromoiodide emulsion containing 2.5 mole percent iodide. The dyes were added to separate portions of the emulsions at the concentrations indicated and the resulting mixtures were coated to obtain a silver coverage of 1.1 g/m² as a cellulose ester support. An example of each coating was exposed in a spectral sensitometer to a quartz-halogen light source through a Wratten 80B color correcting filter, diffraction grating, with filters to remove second order transmission, and superimposed step wedge. The coatings were developed in a Kodak Versamat ® roller transport processor for 80 seconds at 25° C in an Elonhydroquinone developer, fixed, washed and dried. A Density vs. Log Exposure (D Log E) curve was determined for each coating at 400 nm and at each 10 nm interval between 400 and 700 nm. The speed at 0.3 density units above fog was read from each D Log E curve, adjusted for a uniform energy distribution over the spectral range, and plotted against wavelength to obtain a relative log spectral sensitivity curve. The sensitizing maximum and the relative speed at the sensitizing maximum for each dye were determined from this curve.

Results for the dyes prepared in accordance with the number of the examples listed are tabulated below.

Table II

| Dye | Rel. 400nm Speed | Rel. Speed at Sens. Max. | Sensitizing Max. (nm) | Sensitizing Range (nm) | Level (moles/ mole Ag 10⁻⁴) | Fog |
|---|---|---|---|---|---|---|
| Example 30 | 295 | 21 | 570 | 490–650 | 6.0 | .05 |
| Control A | 100 | — | — | 390–490 | — | .04 |
| Control B | 289 | 100 | 600 | 490–670 | 6.0 | .06 |
| Example 29 | 324 | 58**  47 | 520** 480 | 460–590 | 8.0 | .06 |
| Control A | 100 | — | — | 390–490 | — | .06 |
| Control B | 224 | 100 | 600 | 490–660 | 6.0 | .07 |

**Dye has two sensitizing peaks: one at 520nm and one at 480nm
Control A is an undyed coating.
Control B dye was anhydro-3', 9-diethyl-5'-methoxy-5-phenyl-3-(3-sulfobutyl)oxaselenacarbocyanine hydroxide.

The invention has been described in detail with particular reference to certain preferred embodiments thereof, but it will be understood that variations and modifications can be effected within the spirit and scope of the invention.

What is claimed is:

1. A light sensitive silver halide composition spectrally sensitized with a cyanine or merocyanine dye wherein one of the nucleu of said dye is a benzo[a]quinolizinium nucleus or a 6,7-dihydrobenzo[a]quinolizinium nucleus, said cyanine or merocyanine dye being represented by the structural formula:

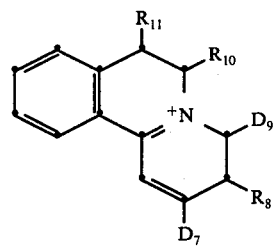

where
  $D_7$ and $D_9$ are, independently, lower alkyl, aryl or the atoms required to complete a cyanine dye having a second nucleus selected from the group consisting of a thiazole nucleus, an oxazole nucleus, a selenazole nucleus, a thiazoline nucleus, a quinoline nucleus, an indole nucleus, a pyridine nucleus, an imidazole nucleus and an imidazoquinoxaline nucleus;
  or a merocyanine dye having a second nucleus selected from the group consisting of a 2-pyrazolin-5-one nucleus, a pyrimidine nucleus, a rhodanine nucleus, a hydantoin nucleus, a thiohydantoin nucleus and an oxazolidinedione nucleus;

provided that at least one of $D_7$ and $D_9$ represents the atoms required to complete a cyanine or merocyanine dye;
  $R_8$ is hydrogen, lower alkyl or aryl; or
  $R_8$ and $D_9$, taken together, complete a fused carbocyclic ring of 5 or 6 carbon atoms or a fused ring having the structure

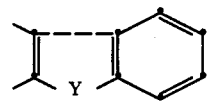

where

Y is 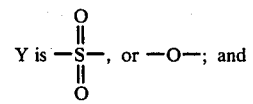

$R_{10}$ and $R_{11}$ are each hydrogen or together form a double bond or a fused benzene ring; or

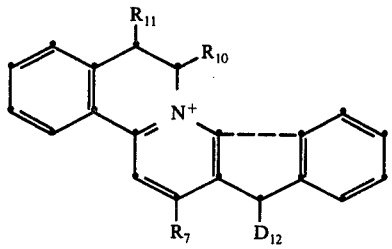

where

R₇ is lower alkyl or aryl;

$R_{10}$ and $R_{11}$ are each hydrogen or together form a double bond or a fused benzene ring; and $D_{12}$ represents the atoms required to complete a cyanine dye having a second nucleus selected from the group consisting of a thiazole nucleus, an oxazole nucleus, a selenazole nucleus, a thiazoline nucleus, a quinoline nucleus, an indole nucleus, a pyridine nucleus, an imidazole nucleus and an imidazoquinoxaline nucleus; or a merocyanine dye having a second nucleus selected from the group consisting of a 2-pyrazolin-5-one nucleus, a pyrimidine nucleus, a rhodanine nucleus, a hydantoin nucleus, a thiohydantoin nucleus and an oxazolidinedione nucleus.

2. A light sensitive silver halide composition containing a methine dye selected from the group consisting of:

(1) 3'-Ethyl-4-methyl-2-benzo[a]quinolizino oxacarbocyanine salt;

(2) 3'-Ethyl-4-methyl-2-benzo[a]quinolizino thiacarbocyanine salt;

(3) 1,3-Diethyl-5-[(4-methylbenzo[a]quinolizidin-2-ylidene)-ethylidene]-2-thiobarbituric acid;

(4) 3'-Ethyl-1,2,3,4-tetrahydro-13-dibenzo[a,f]quinolizino oxacarbocyanine salt;

(5) 3'-Ethyl-2-phenyl-2-benzo[a]quinolizino oxacarbocyanine salt;

(6) 3'-Ethyl-2-phenyl-2-benzo[a]quinolizino thiacarbocyanine salt;

(7) 3-Ethyl-5-[(2-phenyl-4H-benzo[a]quinolizin-4-ylidene)ethylidene]rhodanine;

(8) 1,3-Diethyl-5-[(2-phenyl-4H-benzo[a]quinolizin-4-ylidene)ethylidene]-2-thiobarbituric acid;

(9) 3'-Ethyl-1,2,3,4,6,7-hexahydro-13-dibenzo[a,f]quinolizino thiacarbocyanine salt;

(10) 3'-Ethyl-1,2,3,4,6,7-hexahydro-13-dibenzo[a,f]quinolizino oxacarbocyanine salt; p0 (11) 1,3-Diethyl-5-[(1,2,3,4,6,7-hexahydro-13H-dibenzo[a,f]quinolizin-13-ylidene)ethylidene]-2-thiobarbituric acid;

(12) 3-Ethyl-5-[(1,2,3,4,6,7-hexahydro-13H-dibenzo[a,f]quinolizin-13-ylidene)ethyliden]-2-thiobarbituric acid;

(13) 7-[(3-Ethyl-2-benzothiazolinylidene)ethylidene]-13,14dihydro-6-methyl-7H-benzo[a]indeno[1,2'-f]quinolizinium salt;

(14) 7-[(3-Ethyl-2-benzooxazolinylidene)ethylidene]-13,14-dihydro-6-methyl-7H-benzo[a]indeno[1,2'-f]quinolizinium salt;

(15) Anhydro-3'-(3-sulfopropyl)-1,2,3,4-tetrahydro-5'-methoxy-13-dibenzo[a,f]quinolizino oxacarbocyanine hydroxide; and

(16) 3'-Ethyl-13,14-dihydro-7,7-dioxo-6-dibenzo[a]benzothieno[3,2-f]quinolizino thiacarbocyanine salt.

3. A light sensitive silver halide photographic element comprising a support having thereon at least one layer comprising a light sensitive silver halide composition of claim 1.

4. A light sensitive silver halide photographic element comprising a support having thereon at least one layer comprising a light sensitive silver halide composition of claim 2.

* * * * *